United States Patent
Miczewski et al.

(10) Patent No.: US 7,135,168 B2
(45) Date of Patent: Nov. 14, 2006

(54) HAIR COLOR COMPOSITIONS AND METHODS FOR COLORING HAIR

(75) Inventors: Melissa Jamie Miczewski, Rahway, NJ (US); Lou Ann Christine Vena, Scotch Plains, NJ (US); Saroja Narasimhan, Matawan, NJ (US)

(73) Assignee: Revlon Consumer Products Corporation, New York, NY (US)

( * ) Notice: Subject to any disclaimer, the term of this patent is extended or adjusted under 35 U.S.C. 154(b) by 547 days.

(21) Appl. No.: 10/238,704

(22) Filed: Sep. 10, 2002

(65) Prior Publication Data

US 2004/0045101 A1    Mar. 11, 2004

(51) Int. Cl.
*A61Q 5/10*    (2006.01)
(52) U.S. Cl. ................... 424/70.6; 424/70.31
(58) Field of Classification Search .......... None
See application file for complete search history.

(56) References Cited

U.S. PATENT DOCUMENTS

| | | | | |
|---|---|---|---|---|
| 4,931,066 | A | 6/1990 | Grollier | 8/410 |
| 4,964,874 | A * | 10/1990 | Saphakkul | 8/429 |
| 5,589,177 | A | 12/1996 | Herb | 424/401 |
| 5,688,831 | A | 11/1997 | El-Nokaly | 514/938 |
| 5,702,712 | A | 12/1997 | Wenke | 424/401 |
| 5,931,973 | A | 8/1999 | Malle | 8/431 |
| 5,961,664 | A | 10/1999 | Anderson | 8/405 |
| 5,961,665 | A | 10/1999 | Fishman | 8/406 |
| 5,972,322 | A | 10/1999 | Rath | 424/70.11 |
| 6,106,578 | A | 8/2000 | Jones | 8/406 |
| 6,143,286 | A * | 11/2000 | Bhambhani et al. | 424/70.1 |
| 6,238,653 | B1 | 5/2001 | Narasimhan | 424/62 |
| 6,241,971 | B1 | 6/2001 | Fox | 424/47 |
| 6,284,003 | B1 | 9/2001 | Rose | 8/412 |
| 6,325,995 | B1 | 12/2001 | El-Nokaly | 424/64 |
| 2003/0074746 | A1 | 4/2003 | Fischer | 8/405 |

FOREIGN PATENT DOCUMENTS

| | | |
|---|---|---|
| EP | 312 343 | 4/1989 |
| JP | 01149712 * | 6/1989 |

OTHER PUBLICATIONS

Research Disclosure No. 440111. Improving Color Resistance in Hair Colouring Products. Dec. 2000.
Research Disclosure No. 452082. Hair Color Compositions. Dec. 2001.
Keystone Hair Dyes. Nov. 27, 1999.
Solubilization of Organic Dyes in Microemulsions, Journal Dispersion Science and Technology, vol. 13, No. 6, pp. 611-626 (1992).
Chemistry of Hair Colorant Processes—Science as an Aid to Formulation and Development, Journal of the Society of Cosmetic Chemists, vol. 35, pp. 297-310 (Sep./Oct. 1984).
Diffusion of Semi-Permanent Dyestuffs in Human Hair, Journal of Society of Cosmetic Chemists, vol. 36, pp. 1-16 (Jan./Feb. 1985).
Clairol Loving Car Color Cème, package copy, Jan. 1, 2000.
Cool Hue, Revlon Professional Semi-Permanent Hair Color, Intense Conditioning Shine, package copy, Jan. 1, 2000.
African Pride HiLItes Color Boost, Semi-Permanent Color Enhancer, package copy, Jan. 1, 2000.
Clairol, XTremeFX, Color Shock, Hot Red, package copy, Jan. 1, 2000.

* cited by examiner

*Primary Examiner*—Jyothsna Venkat
(74) *Attorney, Agent, or Firm*—Julie Blackburn

(57) ABSTRACT

A hair color composition comprising, in a polar solvent, association structures having contained therein at least one water soluble or water dispersible dye that is operable to impart color to the hair when contacted therewith and a method for coloring hair.

12 Claims, No Drawings

HAIR COLOR COMPOSITIONS AND METHODS FOR COLORING HAIR

TECHNICAL FIELD

The invention is in the field of compositions for use in coloring hair.

BACKGROUND OF THE INVENTION

More than half of the female population colors their hair. Hair color is used most frequently when individuals age and wish to hide the gray hair that develops as a result of aging. There are generally three types of hair color: permanent, semi-permanent, or temporary. The term "permanent" generally refers to oxidative hair color that bleaches the melanin found in the hair shaft as well as imparting color. The activated peroxide in the oxidative dye composition provides a bleaching effect while the oxidative dye molecules penetrate the hair shaft and polymerize therein. While hair that is oxidatively colored provides a certain permanence, re-coloring every four to six weeks may be necessary due to new hair growth. Oxidative hair color is sold in the form of a two component kit. The reactivity of the oxidative dye and the oxidizing agent means that the two ingredients cannot be formulated into a single composition. Rather, the preferred kits have one container filled with an aqueous composition in the liquid, gel, or creme form that contains the oxidative dyes and a second container filled with a developer composition that contains an oxidizing agent, usually hydrogen peroxide The two containers are combined immediately prior to use and applied to hair. The oxidizing agent and dyes react when mixed. The mixture is applied to hair for an appropriate period of time, generally 20 to 60 minutes, then rinsed off with water. Permanent hair color is very versatile and long lasting in the colors and effects it provides, and it is only with permanent hair color that one can color hair to a shade that is lighter than the natural color Semi-permanent hair color generally provides more lasting color than temporary dyes but without the permanence and commitment of oxidative color. Semi-permanent color is a single component product. Many of such products contain two types of dyes: one of smaller molecular size (such as nitrophenylene diamines and nitroaminophenols) that are capable of penetrating the hair shaft and being retained within. While smaller molecular size permits these dyes to more easily penetrate the hair shaft, this also makes such dyes more vulnerable to washout. The second type of dye used in semi-permanent hair color has a larger molecular size and is too large to penetrate the hair shaft of normal virgin hair. However, such larger dye molecules easily penetrate porous and damaged hair where they are preferentially retained due to their larger size. Accordingly, the balancing of the small and large dye molecules found in many semi-permanent products provides color with a uniform and durable effect Semi-permanent color provides excellent gray blending and good color retention. One big drawback of semi-permanent color is that one cannot color the hair a lighter shade than the starting color. Accordingly, semi-permanent hair color is not an option for dark haired individuals desiring to go blonde.

Temporary hair color is often found in the rinse form, and typically lasts for one shampoo. Such hair color is often used when special effects (such as green hair on St. Patrick's day) is desired. Temporary color simply coats the hair shaft with colorants that are too large to penetrate its outer surface. Minor penetration of the hair shaft may occur in individuals with damaged or porous hair, but such color application rarely lasts through more than one or two shampoos.

While oxidative, or permanent, hair color generally lasts from four to six weeks, within two to three weeks after the oxidative procedure it is common to have color fading in certain areas. In addition, since hair grows about ½ inch a *month*, new hair growth at the roots becomes evident after only a few *weeks*. *In* such *cases*, it is too early and inconvenient to undertake the oxidative dyeing process *again*, or to treat only the faded hairs or new hair growth in a new oxidative *procedure*.

Accordingly, there is a need for a hair color product that enables consumers to touch up hair between permanent hair color procedures with a color that restores color to faded hair and new hair growth. Ideally this composition is in a single use container (no mixing of compositions prior to use required) and will not stain the scalp or surrounding skin. While the desired colorant will not provide permanent coloration, it will be an effective hair colorant for blending in gray and coloring new hair growth. In particular, such composition should provide better wear (increased fade resistance, reduced wash out), and will deposit more dye on the hair (color deposit) when compared to standard compositions. Most desirably, the composition should color the hair in a reduced period of time, say less than about twelve to fifteen, preferably about 10 minutes or less. Such a composition will wash out after a certain number of shampoos enabling use as often as needed without concern for damage to the hair. Because this composition is in a single container it may be used when desired and stored until the container is used up. It eliminates waste.

It is an object of the invention to provide a hair color composition that touch up product that can be used by the consumer as an adjunct to standard hair color to treat hairs that have faded or discolored, or to treat new hair growth, between normal oxidative coloring of the hair.

It is a further object of the invention to provide a hair color composition that optimizes the effects and longevity of hair colored with oxidative hair dye.

It is another object of the invention to provide a hair color composition that has increased fade resistance and reduced wash out when compared to standard hair colorant compositions.

It is a further object of the invention to provide a hair color composition that deposits more color on the hair.

It is a further object of the invention to provide a hair color composition that will color hair in less than about twenty, preferably less than about twelve to fifteen, most preferably about ten, minutes.

It is a further object of the invention to provide a hair color composition that exhibits reduced staining of scalp and surrounding skin.

It is another object of the invention to provide a non-oxidative hair color composition that provides improved wear and fade resistance.

It is another object of the invention to provide a hair color composition that can be applied to dry hair to touch up faded or discolored hair strands that have been previously treated with oxidative dyes, or color new hair growth, between oxidative dyeing procedures.

SUMMARY OF THE INVENTION

The invention is directed to a hair color composition comprising, in a polar solvent, association structures having contained therein at least one water soluble or water dispersible dye that is operable to impart color to the hair when contacted therewith.

The invention is further directed to a semi-permanent hair color composition comprising, in a polar solvent, association structures having contained therein at least one water soluble or dispersible semi-permanent dye wherein said association structures comprise 0.1–99% by weight of the total hair color composition.

The invention is further directed to a method for coloring hair in about less than about fifteen, preferably less than about ten to twelve minutes, by contacting the hair with a hair color composition comprising, in a polar solvent, association structures having contained therein at least one water soluble or dispersible dye.

The invention is further directed to a method for restoring color to dyed hair strands that have faded or discolored, or coloring new hair growth, comprising contacting said faded or discolored strands of hair, or the new hair growth, with a hair color composition comprising, in a polar solvent, association structures having contained therein at least one water soluble or water dispersible dye.

The invention is further directed to a method for touching up the color of oxidatively dyed hair between oxidative dyeing procedures comprising contacting the hair with a hair color composition comprising, in a polar solvent, association structures having contained therein at least one water soluble or water dispersible dye The invention is further directed to a method for reducing the tendency of dyes contained in a hair color composition to stain surrounding skin and scalp during the dyeing procedure by forming the hair color composition of association structures where said dyes are incorporated therein, in a polar solvent.

The invention is also directed to a method for restoring color to faded or discolored strands of hair, or applying color to new hair growth, in hair that has been oxidatively colored, comprising contacting said faded or discolored hair or new hair growth with a semi-permanent hair color composition contained in a single container.

DETAILED DESCRIPTION

The hair color composition of the invention contains at least one water soluble or dispersible dye in aqueous media. The dye is contained within association structures, which are certain molecular structures that are formed in the composition by interaction of certain surfactants and one or more polar solvents that are found therein. The types of association structures will be further described herein and include micelles, liquid crystals, and the like.

The hair color composition may be in aqueous solution or emulsion form. Preferably the composition is in aqueous emulsion form. It may be in the form of a water in oil or oil in water emulsion. The hair color composition will be further described herein, with all percentages referred to being percentages by weight unless otherwise indicated.

A. The Water Soluble or Dispersible Dye

The hair color composition contains at least one, preferably more than one, water soluble or water dispersible dye that is operable to color the hair when contacted therewith. The phrase "operable to color hair when contacted therewith" means, in the most preferred embodiment of the invention, that the dye alone, without combining with any additional activators or accelerators, will color the hair (as opposed to certain types of oxidative dyes which must be combined with an activator in order to impart color to the hair fiber).

A variety of dyes are suitable including direct dyes, disperse dyes, acid dyes, basic, dyes, direct, dyes, and so on. Suitable amounts of dye preferably range from about 0.001–20%, preferably about 0.005–15%, more preferably about 0.010–10% by weight of the total composition. Preferred are the compounds that fall into the general category of semi-permanent dyes. Examples of such dyes are set forth below:

1. Basic Dyes

Suitable basic dyes include blues, browns, greens, oranges, reds, and yellows. Suitable blues include Basic Blue 3, 6, 7, 9, 26, 41, 47, and 99. Suitable browns include Basic Browns 4, 16, and 17. Suitable greens include Basic Green 1 and 4. Suitable oranges include Basic Orange 1 and 2 Suitable Reds include Basic Red 1, 2, 22, 46, 76, and 118. Suitable violets include Basic Violet 1, 3, 4, 10, 11:1, 14, and 16. Suitable yellows include Basic Yellow 11, 28, and 57.

Suitable basic dyes for use in the claimed compositions are set forth in the CTFA Cosmetic Ingredient Handbook, Eighth Edition, pages 117–124, which are hereby incorporated by reference in their entirety.

2. HC Dyes

Also suitable for use in the compositions are various HC dyes such as blue, brown, green, orange, red, violet, and yellow. Suitable blues include HC Blue 2, 4, 5, 6, 7, 8, 9, 10, 11, 12, 13, and 14. Suitable browns include HC Brown 1 and 2 Suitable greens include HC Green 1. Suitable oranges include HC Orange 1, 2, 3, and 5 Suitable reds include HC Red 1, 3, 7, 8, 9, 10, 11, 13, and 14. Suitable violets include HC Violet 1 and 2. Suitable yellows include HC Yellow 2, 4, 5, 6, 7, 8, 9, 10, 11, 13, 14, and 15. Such HC dyes are set forth on pages 615–623 of the CTFA Cosmetic Ingredient Handbook, Eighth Edition, 2000, which is hereby incorporated by reference in its entirety.

3. Acid Dyes

Also suitable for use in the compositions are various acid dyes such as black, blue, brown, green, orange, red, violet, and yellow. Examples of Acid Black are numbers 1 and 52. Suitable blues include Acid Blue 1, 3, 9, 62, and 74, including Lakes thereof. Examples of browns and greens include Acid Brown 13 and Acid Green 1, 25, and 50, respectively. Suitable oranges include Acid Orange 3, 6, 7, and 24. Suitable reds include Acid Red 14, 18, 27, 33, 35, 51, 52, 73, 87, 92, 95, 184, and 195. Suitable violets include Acid Violet 9 and 43. Suitable yellows include Acid Yellow 1, 3, 23, and 73. In each case the dyes may be Lakes thereof. Such Acid dyes are set forth on pages 13–23 of the CTFA Cosmetic Ingredient Handbook, Eighth Edition, 2000, which is hereby incorporated by reference in its entirety.

4. Direct and Disperse Dyes

Also suitable are various types of dyes referred to as direct dyes or disperse dyes. Suitable direct dyes include Direct Black 51, Direct Blue 86, Direct Red 23, 80, and 81; Direct Violet 48, and Direct Yellow 12. Such direct dyes are set forth on pages 469–471 of the CTFA Cosmetic Ingredient Handbook, Eighth Edition, 2000, which is incorporated by reference in its entirety.

Suitable disperse dyes include Disperse Black 9, Disperse Blue 1, 3, and 7; Disperse Brown 1, Disperse Orange 3, Disperse Red 11, 15, and 17; and Disperse Violet 1, 4, and 15. Such disperse dyes are as set forth on 491–493 of the CTFA Cosmetic Ingredient Handbook, Eighth Edition, 2000, which is hereby incorporated by reference in its entirety.

In the preferred embodiment of the invention, HC dyes and the Disperse dyes are used.

C. Association Structures

The dye ingredients mentioned above are incorporated into the association structures that form the claimed aqueous based composition. Preferably the composition comprises about 0.01–100%, preferably about 0.05–99%, more preferably about 0.1–95% by weight of the total composition of association structures having the water soluble or dispersible dyes contained therein. The composition is preferably a liquid or creme at room temperature (25° C.).

The term "association structures" when used herein means micelles or liquid crystals that are formed by the interaction of at least one surfactant and at least one polar solvent. The association structures may be formed at room temperature or upon application of heat.

1 Types of Association Structures (a). Liquid Crystals

The term "liquid crystal" or "liquid crystal state" is an intermediate, or mesomorphic state of matter between liquid and solid. In the liquid state the molecules present in a composition are generally in random orientation. In the solid state, the molecules present are in a very ordered configuration The liquid crystalline state occurs when the molecules present in the composition exhibit intermediate stages of order. More specifically, this may occur when certain amphiphilic ingredients present in the polar solvent-containing composition align in a head-to-head/tail-to-tail configuration therein to form certain types of molecular arrangements. By "head-to-head/tail-to-tail" is meant that the hydrophilic portions of the amphiphilic surfactant are attracted to each other and the lipophilic portions are also attracted to each other such that the surfactant molecules will form a certain molecular order within the composition, which is somewhere between the completely disordered liquid state and the completely ordered solid state.

When the surfactant molecules are oriented in such a manner, certain active ingredients found within the composition will be enclosed within the molecular arrangements formed by the oriented molecules. This in turn provides unique properties to the composition.

Liquid crystalline phases are generally named according to their degree of molecular ordering. The general stages of order are (1) isotropic—random ordering of molecules (2) nematic ordering—molecules are orientationally ordered, or in a generally parallel configuration in one dimension, (3) smectic ordering—molecules are orientationally ordered in two dimensions, and (4) crystal—completely oriented solid state. Smectic liquid crystals are given the designation "S" and can be further classified into subcategories A–H based upon their degree of ordering. For example, the smectic B phase (SB) is a disordered crystal where the molecules are arranged in hexagonal arrangement and the positions of the hexagonal nets within each layer repeat in a regular manner throughout the phase.

Suitable smectic liquid crystals for use as carriers for the dyes in the claimed compositions include smectic types A–H. Preferably the smectic liquid crystals A–H are lyotropic, meaning that they are formed in a polar solvent.

Further preferred is where the hydrophilic groups have hydrogen bonded causing the molecules to laterally and cooperatively to form head-to-head and tail-to-tail bilayers. More preferably, the liquid crystals found in the compositions of the invention are in the rod or vesicle form and exhibit a generally lamellar configuration Also suitable are nematic liquid crystals, which have no subcategories, and are referred to by the designation "N". Such nematic liquid crystals are also suitable as carriers for the dyes in the claimed composition. Preferably the nematic liquid crystals are lyotropic. Obviously excluded are the isotropic and crystalline states which represent the disordered molecular orientation and the completely molecularly ordered state respectively.

As discussed above, the liquid crystals are formed by the combination of certain amphiphilic surfactants in a polar solvent. Suitable amphiphilic surfactants and polar solvents will be further discussed below.

(b) Micelles

The dye ingredients in the claimed compositions may be encapsulated within association structures in the micelle form. Micelles are assemblies of amphiphilic molecules whose polar head groups are exposed to water and whose aliphatic or lipophilic side chains are oriented toward a hydrophobic interior More particularly, in an emulsion having a dispersed lipophilic phase and an aqueous continuous phase, the lipophilic portion of the amphiphilic molecule will orient at the surface of the dispersed oil droplets and the hydrophilic portion will orient toward the continuous water phase.

Reverse micelles are found in water in oil emulsions and occur when the polar head groups of the amphiphilic material orient toward the dispersed water droplets and the lipophilic portions toward the continuous lipophilic phase.

The emulsions formed may be in the microemulsion form where the dispersed phase droplets are very small, generally from about 100 to 1500, preferably 200 to 1000, more preferably 250 to 700 Angstroms (Å) Preferably, the micelle association structures in the claimed composition are reverse micelles and formed in a water in oil emulsion.

(c). Other Association Strucures

Other association structures that may be used as a carrier for the dye ingredients in the claimed composition include liposomes, vesicles, and the like. Liposomes are microscopic spherical vesicles formed when phospholipids are hydrated in a polar solvent such as water 2. Formation of Association Structures The association structures in the claimed composition are formed when certain amounts of one or more surfactants are combined with one or more polar solvents. In order to optimize the formation of association structures certain other lipophilic ingredients may be added to the mixture.

(a) Surfactants

Any surfactant that is capable of forming association structures in polar solvent at a temperature ranging from about 20 to 60° C., preferably about 25 to 40° C., is acceptable. The surfactant may be anionic, cationic, nonionic, amphoteric, or zwitterionic. Generally the amount of the surfactant required will depend on the other ingredients present in the composition, but may preferably range from about 0.001–50%, preferably about 0.005–45%, more preferably about 0.01–40% by weight of the total composition Typically surfactants that will form association structures are organic, amphiphilic, surface active ingredients that will form a certain molecular order in a polar solvent, or aqueous phase having the hair color ingredients contained therein. The term "amphiphilic" means that the surface active material contains both lipophilic and hydrophilic portions such that the hydrophilic portion of the molecule is attracted to, and orients with, the polar, aqueous phase ingredients in the composition, and the lipophilic portion of the molecule is attracted to, and orients with the nonpolar phase of the composition. Examples of radicals that will confer hydrophilicity include hydroxy-polyethyleneoxy, hydroxyl, carboxylates, sulfonates, sulfates, phosphates, or amines. Examples of radicals that will confer lipophilicity are $C_{1-40}$ straight or branched chain alkyl, fluoro, aryl, aryloxy, $C_{1-40}$ hydrocarbyl acyl, hydroxy-polypropyleneoxy, or mixtures thereof. The $C_{1-40}$ alkyl may be non-interrupted, or interruped by one or more oxygen atoms, a benzene ring, amides, esters, or other functional groups. Examples of suitable organic, amphiphilic, surface active agents include nonionic, amphoteric, cationic, and anionic surface active agents. The organic, amphiphilic, surface active agent may be a liquid, semi-solid, or solid at room temperature.

(i) Nonionic Surfactants

A variety of nonionic surface active agents may be used in the claimed compositions. Preferably, such surface active agents HLB (hydrophile/lipophile balance) of about 12–20, more preferably about 13–16. Nonlimiting examples of nonionic surfactants include Alkoxylated Alcohols Suitable alkoxylated alcohols include ethers formed from the reaction of an aliphatic, aromatic, or heterocyclic alcohol with an alkylene oxide, generally ethylene or propylene oxide. Preferably, the alcohol is an aliphatic alcohol, more preferably a fatty alcohol having 10–22 carbon atoms; and the alkylene oxide is ethylene oxide. Examples of preferred alkoxylated alcohols include steareth, ceteth, ceteareth, beheneth, and the like, having from 1 to 200 repeating ethylene oxide units, as well as PEG derivatives of fatty acids such as PEG dioleate, PEG distearate, PEG isostearate, and so on.

Sorbitan Derivatives

Suitable sorbitan derivatives are esters or ethers or sorbitan, which is a heterocyclic ether formed by the dehydration of sorbitol. Sorbitan may be derivatized by ethoxylation and/or esterification of the hydroxyl groups. Suitable acids used for esterification include C1–30 acids, more preferably, fatty acids having 6–22 carbon atoms. Examples of suitable sorbitan derivatives include PEG derivatives of sorbitan wherein the number of repeating ethylene oxide units ranges from 2 to 200, such as PEG sorbitan beeswax, glyceryl/sorbitol/oleate/hydroxystearate, PEG sorbitan cocoate, PEG sorbitan diisostearate, PEG sorbitan isostearate, PEG sorbitan lanolate, PEG sorbitan laurate, PEG sorbitan oleate, PEG sorbitan palmitate, PEG sorbitan perisostearate, PEG sorbitan peroleate, PEG sorbitan stearate, PEG sorbitan tetraoleate, PEG sorbitan tetrastearate, PEg sorbitan triisostearate; Polysorbates such as Polysorbate 20–85, Polysorbate 80 acetate; and sorbitan esters such as sorbitan caprylate, cocoate, diisostearate, dioleate, distearate, isostearate, laurate, oleate, olivate, palmitate, sesquiisostearate, sesquioleate, sesquistearate, stearate, triisostearate, trioleate and the like Glyceryl Ethers Also suitable are linear or branched ethers of polyglycerol having the general formula:

R-(Gly)$_n$-OH wherein n is 1–10 and R is a straight or branched, saturated or unsaturated alkyl having 6 to 30 carbon atoms, and Gly is the glycerol residue. Examples of suitable polyglyceryl derivatives include polyglyceryl decaoleates, polyglyceryl caprates, polyglyceryl diisostearates, polyglyceryl distearates, polyglyceryl isopalmitates, polyglyceryl laurates, and the like Glyceryl Esters Suitable glyceryl esters include alkoxylated glyceryl esters include synthetic or semi-synthetic glyceryl esters, e.g fatty acid mono-, di-, and triglycerides which are natural fats or oils that have been modified, for example, by reaction with alkylene oxide units, preferably ethylene oxide units. Examples of such glyceryl esters include PEG glyceryl oleates, PEG glyceryl stearates and isostearates, PEG glyceryl laurates, PEG glyceryl tallowates, and so on. Preferred PEG glyceryl esters include those of the formula RC(O)OCH$_2$CH(OH)CH$_2$(OCH$_2$CH$_2$)$_n$OH wherein n is 5–200 and RC(O)— is a hydrocarbylcarbonyl group wherein R is preferably an aliphatic radical having 7 to 19 carbon atoms.

Also suitable are glyceryl esters formed by the reaction of glycerol with one or more fatty acids. Examples of these glyceryl esters include glyceryl adipate, caprylate, cocoate, stearate, diisostearate, laurate, linoleate, and so on.

Dialkyl Sulfoxides

Also suitable are long chain dialkyl sulfoxides containing one short chain alkyl or hydroxy alkyl radical of from about 1 to 3 carbon atoms and one long hydrophobic chain which may be an alkyl, alkenyl, hydroxyalkyl, or ketoalkyl radical containing from about 8 to 20 carbon atoms, from 0 to 10 ethylene oxide moieties, and 0 or 1 glyceryl moiety Polyethylene Oxide Condensates of Alkyl Phenols Suitable condensates include the condensation products of alkyl phenols having an alkyl group of 6 to 20 carbon atoms with ethylene oxide being present in amounts of about 10 to 60 moles of ethylene oxide per mole of alkyl phenol.

Condensation Products of Ethylene Diamine

Examples of suitable condensation products of ethylene diamine include products of ethylene oxide with the reaction product of propylene oxide and ethylene diamine.

Long Chain Tertiary Amine Oxides

Preferred long chain tertiary amine oxides include those corresponding to the general formula:

R$_1$R$_2$R$_3$NO wherein R$_1$ contains an alkyl, alkenyl or monohydroxyalkyl radical ranging from about 8 to 18 carbon atoms in length, from 0 to about 10 ethylene oxide moieties, and from 0 to about 1 glyceryl moiety and R$_2$ and R$_3$ are each alkyl or monohydroxyalkyl groups containing from about 1 to about 3 carbon atoms.

Long Chain Tertiary Phosphine Oxides

Suitable long chain tertiary phosphine oxides include those corresponding to the general formula:

RR$_1$R$_2$PO wherein R contains an alkyl, alkenyl, or monohydroxyalkyl radical having 8 to 18 carbon atoms, from 0–10 ethylene oxide moieties and 0 or 1 glyceryl moiety, and $R_2$ and $R_3$ are each alkyl or monohydroxyalkyl group containing from about 1 to 3 carbon atoms.

Polyhydroxyl Fatty Acid Amides

Examples of $C_{10-18}$ alkyl($C_{1-6}$)polyhydroxy fatty acid amides such as $C_{12-18}$ methylglucamides, N-alkoxy polyhydroxy fatty acid amides, N-propyl through N-hexyl $C_{12-18}$ glucamides and so on.

Alkyl Polysaccharides

Suitable nonionic surfactants are alkyl polysaccharides, or alkyl glycosides, disclosed in U.S. Pat. Nos. 5,716,418 and 5,756,079, both of which are hereby incorporated by reference. These alkylglycosides have the general formula:

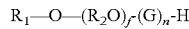
$R_1$—O—$(R_2O)_t$-$(G)_n$-H wherein $R_1$ is a linear or branched alkyl or alkenyl radical having 12 to 30 carbon atoms, $R_2$ is a $C_{2-4}$ alkylene, (G) is an anhydroglucose unit, t is a number between 0 and 10, preferably 0 to 4, and n is a number from about 1 to 15. Examples of such alkyl polysaccharides are octyl, nonydecyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses, and so on. Certain polyglycosides having the above formula are sold by Henkel Corporation under the tradenamnes APG 300, APG 350, APG 500, APG 550, APG 625, or the tradename Planteren, e.g. Planteren 300, 600, 1200, 2000, and so on.

Particularly preferred nonionic surfactants for use in the claimed compositions are alkoxylated alcohols, glyceryl esters, and polyethylene glycol derivatives of fatty acids.

(ii) Anionic Surfactants

Also suitable for use as the amphiphilic surface active material are one or more anionic surfactants.

Alkyl Sulfates

Anionic surfactants include alkyl and alkyl ether sulfates generally having the formula $ROSO_3M$ and $RO(C_2H_4O)_xSO_3M$ wherein R is alkyl or alkenyl of from about 10 to 20 carbon atoms, x is 1 to about 10 and M is a water soluble cation such as ammonium, sodium, potassium, or triethanolamine cation.

Another type of anionic surfactant which may be used in the compositions of the invention are water soluble salts of organic, sulfuric acid reaction products of the general formula:

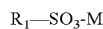
$R_1$—$SO_3$-M wherein $R_1$ is chosen from the group consisting of a straight or branched chain, saturated aliphatic hydrocarbon radical having from about 8 to about 24 carbon atoms, preferably 12 to about 18 carbon atoms; and M is a cation. Examples of such anionic surfactants are salts of organic sulfuric acid reaction products of hydrocarbons such as n-paraffins having 8 to 24 carbon atoms, and a sulfonating agent, such as sulfur trioxide.

Fatty Acids Esterified with Isethionic Acid

Also suitable as anionic surfactants are reaction products of fatty acids esterified with isethionic acid and neutralized with sodium hydroxide. The fatty acids may be derived from coconut oil or other similar vegetable or animal derived oils that contain fatty acids Succinates or Succinimates In addition, succinates and succinimates are suitable anionic surfactants This class includes compounds such as disodium N-octadecylsulfosuccinate; tetrasodium N-(1,2-dicarboxyethyl)-N-octadecylsulfosuccinate; and esters of sodium sulfosuccinic acid e g. the dihexyl ester of sodium sulfosuccinic acid, the dioctyl ester of sodium sulfosuccinic acid, and the like.

Olefin Sulfonates

Other suitable anionic surfactants include olefin sulfonates having about 12 to 24 carbon atoms. The term "olefin sulfonate" means a compound that can be produced by sulfonation of an alpha olefin by means of uncomplexed sulfur trioxide, followed by neutralization of the acid reaction mixture in conditions such that any sultones which have been formed in the reaction are hydrolyzed to give the corresponding hydroxy-alkanesulfonates. The alpha-olefin from which the olefin sulfonate is derived is a mono-olefin having about 12 to 24 carbon atoms, preferably about 14 to 16 carbon atoms.

Other classes of suitable anionic organic surfactants are the beta-alkoxy alkane sulfonates or water soluble soaps thereof such as the salts of $C_{10-20}$ fatty acids, for example coconut and tallow based soaps. Preferred salts are ammonium, potassium, and sodium salts N-acyl Amino Acids Still another class of anionic surfactants include N-acyl amino acid surfactants and salts thereof (alkali, alkaline earth, and ammonium salts) having the formula:

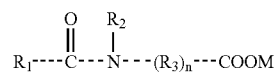

wherein $R_1$ is a $C_{8-24}$ alkyl or alkenyl radical, preferably $C_{10-18}$; $R_2$ is H, $C_{1-4}$ alkyl, phenyl, or —$CH_2COOM$; $R_3$ is $CX_2$— or $C_{1-2}$ alkoxy, wherein each X independently is H or a $C_{1-6}$ alkyl or alkylester, n is from 1 to 4, and M is H or a salt forming cation as described above. Examples of such surfactants are the N-acyl sarcosinates, including lauroyl sarcosinate, myristoyl sarcosinate, cocoyl sarcosinate, and oleoyl sarcosinate, preferably in sodium or potassium forms (iii) Cationic, Amphoteric, or Zwitterionic Surfactants Certain types of amphoteric, zwitterionic, or cationic surfactants may also be used as the amphiphilic surface active material. Descriptions of such surfactants are set forth in U.S. Pat. No. 5,843,193, which is hereby incorporated by reference in its entirety.

(b) Polar Solvents

A variety of polar solvents may be suitable including water, mono-, di-, or polyhydric alcohols, and similar water soluble ingredients. Typically the claimed compositions comprise from about 0.1–99.9%, preferably about 5–95%, more preferably about 10–90% by weight of the total composition of polar solvent which includes water.

Other suitable non-aqueous Suitable monohydric alcohols include ethanol, isopropanol, benzyl alcohol, butanol, pentanol, ethoxyethanol, and the like. Examples of dihydric, or polyhydric alcohols, as well as sugars and other types of humectants that may be used include glucose, fructose, mannose, mannitol, malitol, lactitol, inositol, and the like. Suitable glycols include propylene glycol, butylene glycol, ethylene glycol, polyethylene glycols having from 4 to 250 repeating ethylene glycol units, ethoxydiglycol, and the like. Many of these types of alcohols serve also serve as penetration enhancers, meaning that they enhance penetration of the dyes into the hair shaft by virtue of their tendency to act as humectants and swell the hair shaft. Ethoxydiglycol is a particularly good penetration enhancer.

In the preferred embodiment of the invention the composition comprises water in addition to one or more polar solvents which are dihydric alcohols. In the preferred compositions, about 0.001–20%, preferably about 0.005–10%, more preferably about 0.001–8% by weight of the total composition is a non-aqueous polar solvent.

(c) Lipophilic Materials

Preferably, certain lipophilic materials are used in addition to the surfactants and polar solvents to form the association structures. Preferred lipophilic materials include:

(i). Fatty Acids

In the preferred embodiment of the invention the claimed composition contains one or more fatty acids. Suitable fatty acids are carboxylic acids having the general formula R—COOH wherein R is a straight or branched chain, saturated or unsaturated alkyl having about 7 to 30 carbon atoms. Suggested ranges of fatty acid, if present, are about 0.01–25%, preferably about 0.05–20%, preferably about 0.1–15% by weight of the total composition. Suitable fatty acids include oleic, palmitic, arachidic, arachidonic, behenic, capric, caproic, capryllic, coconut, tallow, lauric, linoleic, linolenic, myristic, pelargonic, ricinoleic, stearic, undecylenic, and so on. Particularly preferred is oleic acid, an unsaturated fatty carboxylic acid The fatty acids aid in the formation of liquid crystals.

(ii). Fatty Alcohols

One or more fatty alcohols may be included in the composition. Fatty alcohols exhibit the general formula R—CH$_2$OH where R is a straight or branched chain, saturated or unsaturated alkyl having about 7 to 30 carbon atoms. Suggested ranges of fatty alcohols, if present, are about 0 001–15%, preferably about 0.005–10%, preferably about 0.01–8% by weight of the total composition. Examples of suitable fatty alcohols include arachidyl alcohol, C9–11 alcohols, C12–13 alcohols, C12–15 alcohols, C12–16 alcohols, C14–15 alcohols, caprylic alcohol, cetearyl alcohol, cetyl alcohol, coconut alcohol, decyl alcohol, palm alcohol, lauryl alcohol, myristyl alcohol, oleyl alcohol, tallow alcohol, tridecyl alcohol, and mixtures thereof. Particuarly preferred is oleyl alcohol, cetearyl alcohol, and mixtures thereof.

3. Benefits of Association Structures

The formation of association structures having the water soluble or dispersible dyes contained therein provides a number of benefits. Such compositions exhibit reduced staining to surrounding skin and scalp during the dye process. It is well known that when coloring the hair, if dyes accidentally spill on the skin a noticeable stain will result. In some cases the dyes present will also stain the scalp. Without being bound by this explanation, it is believed that the encapsulation of the dyes within the association structures better targets the dyes to the hair shaft because they are preferentially absorbed into the hair shaft leaving the lipophilic ingredients or portions of ingredients present remain on the hair and to some extent coat the surrounding skin to reduce the potential for staining. This serves the dual purpose of reducing the tendency of the dyes to color the skin as well as providing a conditioning effect to the hair.

Another benefit of encapsulating the dyes within association structures is that the composition provides a much more conditioning effect to the hair. The lipophilic ingredients or portions thereof in the composition deposit on the hair shaft and provide a fine layer of lipophilic material thereon.

The presence of association structures also improves color deposit on the hair. In other words more of the dye actually reaches the hair shaft and stays there. This makes the compositions more effective colorants. In addition the claimed compositions also provide improved fade resistance to the colored hair. When the hair is colored with the composition, the color will not wash out as quickly. It is not certain whether this is due to the improved deposit of the dyes on the hair or the improved affinity of the deposited dye molecules to the hair shaft.

Another benefit when the dyes contained within the association structures is the very significant reduction in the time required to color the hair Typically, when semi-permanent dyes are used, it takes at least 20 to 40 minutes to color the hair. The claimed compositions can readily color the hair in about ten to twelve minutes or less and the amount of color deposit is the same as found with a 20 to 40 minute procedure. This makes the claimed compositions particularly useful as a hair color touch up. In particular, when individuals regularly dye their hair with oxidative dyes, discoloration or color fading of strands of hair are sometimes noted particularly around the temples or hairline. In addition, new hair growth at the roots is noticed within a few weeks. The claimed composition can be incorporated into an appropriate dispenser and applied to the hairs that have become discolored or faded and the new hair growth. Most conveniently, the composition can be applied directly to dry hair. The color will develop in about ten to twelve minutes or less. The individual then simply rinses the hair with water or shampoos the hair to remove the extraneous color. The resulting hair strands have then been restored to the desired color.

In the most preferred embodiment of the invention, the dyes used do not involve mixing with activators to achieve results, but rather are found in the single container. The composition can be filled into single or multiple use containers and can be stored between usages if desired The consumer can simply buy a container of the composition, use it as needed, and when it is empty discard it eliminating waste. It is envisioned that the consumer who oxidatively colors her hair every four to six weeks can purchase a single or multiple use container of the dye composition of the invention which has the same or very similar shade as the color used to oxidatively dye the hair. When some color fading of the oxidative dye appears, or when new hair growth becomes evident, the consumer can simply apply the desired amount of the composition to the select hair strands or roots of dry hair, wait about ten minutes, then rinse the composition out of the hair by shampooing in the shower or in any other manner. The faded hair strands and new growth are colored back to the original oxidatively colored shade in a very simple, convenient procedure.

D. Other Ingredients

The compositions of the invention may be in the solution or emulsion form, and will contain a variety of other ingredients to enhance the beneficial properties of the composition, as further described herein.

1. Thickening Agents

In the preferred embodiment of the invention, the composition may contain one or more agents that will provide a thickening, or viscosity increasing, effect to the compositions. Suitable thickening agents include synthetic metal silicates, acrylate copolymers, cellulose polymers, and the like. Particularly preferred are alkali metal or alkaline earth metal silicates. Suitable alkali metals or alkaline earth metals include sodium, potassium, magnesium, lithium, and the like either alone or in combination with aluminum. Suggested ranges are from about 0.001–20%, preferably about 0.005–15%, preferably about 0.01–12% by weight of the total composition. Particularly preferred is Veegum, a magnesium aluminum silicate sold by Vanderbilt Chemical 2. Preservatives The composition preferably contains one or more preservatives. Suggested ranges are about 0 0001–8%, preferably 0.0005–7%, more preferably about 0.001–5% by weight of the total composition. Suitable preservatives include methyl, ethyl, and propyl paraben, hydantoins, and the like.

3. Chelating Agents

The composition may also contain 0.0001–5%, preferably 0.0005–3%, more preferably 0.001–2% of one or more chelating agents which are capable of complexing with and inactivating metallic ions in order to prevent their adverse effects on the stability or effects of the composition. In particular, the chelating agent will chelate the metal ions found in the water and prevent these ions from interfering with the deposition and reaction of the dye with the hair fiber surface. Suitable chelating agents include EDTA and calcium, sodium, or potassium derivatives thereof, HEDTA, sodium citrate, TEA-EDTA, and so on.

4. pH Adjusters

It may also be desireable to add small amounts of acids or bases to adjust the pH of the composition to the desired pH range of 7.1 to 11. Suitable acids include hydrochloric acid, phosphoric acid, erythorbic acid, and the like Suitable bases include sodium hydroxide, potassium hydroxide, and the like. Also suitable are primary, secondary, or tertiary amines or derivative thereof such as aminomethyl propanol, monoethanolamine, and the like. Suggested ranges of pH adjusters are from about 0.00001–8%, preferably about 0.00005–6%, more preferably about 0 0001–5% by weight of the total composition The compositions of the invention may be applied to the whole head or strands that the individual desires to color. In the preferred embodiment of the invention, the dyes used are semi-permanent and will last anywhere from about six to twenty four shampoos.

The invention will be further described in connection with the following examples which are set forth for the purpose of illustration only

EXAMPLE 1

Hair color compositions according to the invention were prepared as follows:

| Ingredient (%) | Medium Brown | Light Auburn | Dark Brown/Black |
|---|---|---|---|
| Water | 70.85 | 73.294 | 69.145 |
| Ethoxydiglycol | 5.00 | 5.00 | 5.00 |
| Methylparaben | 0.20 | 0.20 | 0.20 |
| Disodium EDTA | 0.05 | 0.05 | 0.05 |
| Aminomethyl propanol | 3.60 | 3.60 | — |
| Monoethanolamine | — | — | 3.60 |
| Erythorbic acid | 0.06 | 0.06 | 0.06 |
| HC Yellow #2 | 0.43 | 0.126 | 0.86 |
| HC Yellow #4 | 0.43 | 0.33 | 0.805 |
| HC Red #3 | 0.15 | 0.28 | 0.10 |
| HC Blue CP | 1.97 | — | 1.97 |
| HC Red 13 | 0.30 | — | 0.25 |
| Disperse Orange #3 | — | 0.60 | — |
| HC Violet 1, 3 bis | — | — | 1.00 |
| Veegum | 1.00 | 0.50 | 1.00 |
| Oleic acid | 9.38 | 9.38 | 9.38 |
| Cetearyl alcohol | 3.00 | 3.00 | 3.00 |
| Polawax | 1.50 | 1.50 | 1.50 |
| Oleth-20 | 0.75 | 0.75 | 0.75 |
| Steareth-21 | 0.53 | 0.53 | 0.53 |
| Oleyl alcohol | 0.30 | 0.30 | 0.30 |
| Fragrance | 0.50 | 0.50 | 0.50 |

The compositions were prepared by placing the water in a beaker having a homogenizer mill attached and heating to 70–75° C. The homogenizer mill was then turned on and the veegum sprinkled into the beaker. The mixture was milled for 15 minutes. While maintaining the temperature, ethoxydiglycol, disodium EDTA, erythorbic acid and methylparaben were added to mixture, which was further milled for about 15 minutes The dyes were then added to the mixture. In a separate beaker the aminomethylpropanol, monoethanolamine, and water were combined, then this mixture was added to the mixture of other ingredients in the beaker. The composition was further milled for 30 minutes to ensure that the dyes were completely solubilized. The batch was transferred to a turbine/sweep kettle.

Separately, the oil ingredients—oleic acid, cetearyl alcohol, emulsifying wax, oleth-20, oleyl alcohol, and steareth-21—were combined and heated to 70–75° C. The oil phase was then combined with the other ingredients and mixed well while maintaining the temperature at 70–75° C. The batch was cooled to 35–40° C. The fragrance oil was added and the composition mixed for an additional 15 minutes. The batch was cooled to 25° C.

The compositions were observed under an optical microscope in polarized light and lamellar liquid crystal association structures in the lamellar were observed for all colors.

EXAMPLE 2

Comparative formulas were prepared where the liquid crystal forming ingredients were removed from the compositions and replaced with water. The comparative formulations are set forth below:

| Ingredient (%) | Medium Brown Comparative | Light Auburn Comparative | Dark Brown/ Black Comparative |
| --- | --- | --- | --- |
| Water | 76.93 | 79.374 | 75.225 |
| Ethoxydiglycol | 5.00 | 5.00 | 5.00 |
| Methylparaben | 0.20 | 0.20 | 0.20 |
| Disodium EDTA | 0.05 | 0.05 | 0.05 |
| Aminomethyl propanol | 3.60 | 3.60 | — |
| Monoethanolamine | — | — | 3.60 |
| Erythorbic acid | 0.06 | 0.06 | 0.06 |
| HC Yellow #2 | 0.43 | 0.126 | 0.86 |
| HC Yellow #4 | 0.43 | 0.33 | 0.805 |
| HC Red #3 | 0.15 | 0.28 | 0.10 |
| HC Blue CP | 1.97 | — | 1.97 |
| HC Red 13 | 0.30 | — | — |
| Disperse Orange #3 | — | 0.60 | — |
| HC Violet 1, 3 bis | — | — | 1.00 |
| Veegum (magnesium aluminum silicate) | 1.00 | 0.50 | 1.00 |
| Oleic acid | 9.38 | 9.38 | 9.38 |
| Cetearyl alcohol | — | — | — |
| Polawax (emulsifying wax) | — | — | — |
| Oleth-20 | — | — | — |
| Steareth-21 | — | — | — |
| Oleyl alcohol | — | — | — |
| Fragrance | 0.50 | 0.50 | 0.50 |

The compositions were prepared by first heating the water in a kettle having a homogenizer mill attached, to a temperature of about 70 to 75° C. The mill was then turned on and the magnesium aluminum silicate sprinkled in and mixed well for 15–30 minutes. After the magnesium aluminum silicate was hydrated, the mill was turned off. While maintaining the temperature, the ethoxydiglycol, disodium EDTA, erythorbic acid, and methyl paraben were added to the main beaker and mixed for 15 minutes. The dyes were then added. In a side kettle the aminomethylpropanol and monoethanolamine were mixed with a small amount of the water. This pre-mix was then added to the ingredients in the main kettle and mixed for 30 minutes to ensure that the dyes were completely solubilized. The mill was turned off and the batch transferred to a turbine/sweep kettle. The batch was cooled to 35–40° C. and the fragrance oil added. The mixture was further mixed for an additional 15 minutes and cooled to 28–32° C.

EXAMPLE 3

About 0.05 grams of each composition was placed on a glass slide and observed under an optical microscope in polarized light at 20× magnification. Photographs were taken using an Image Pro Plus Version 4.1.0.9 (Serial No. 41N400000-13847) using an Olympus BX 60 microscope. All of the Example 1 compositions exhibited association structures in the liquid crystal, lamellar form. None of the Example 2 compositions exhibited any sign of association structures.

EXAMPLE 4

Ten grams of the medium brown hair color composition of Example 1 ("Medium Brown Test") and the medium brown comparative hair color composition ("Medium Brown Comparative") of Example 2 were applied to 95% gray hair swatches weighing 1.5 grams each. Five swatches per composition were treated. The compositions were applied to the hair for 10 minutes and rinsed with water. One swatch colored with each composition was shampooed with Revlon Flex Extra Body shampoo for 30 seconds once, and the others 4, 8, 12, and 24 times respectively. The swatches were compared visually and the overall change in color, ΔE which was calculated according to the following formula:

$$\Delta E = \sqrt{(L-L_o)^2 + (a-a_o)^2 + (b-b_o)^2}$$

wherein L is the is the level of darkness or lightness, a is the red and green components, and b is yellow and blue components, and wherein the subscript o means prior to dyeing. All of L, a, and b, were measured using a DataColor colorimeter. The results are as follows:

| Medium Brown Test | | | | | | Medium Brown Comparative | | | | | |
| --- | --- | --- | --- | --- | --- | --- | --- | --- | --- | --- | --- |
| Wash | L | ΔL | a | b | ΔE | Wash | L | ΔL | a | b | ΔE |
| 1 | 43.55 | | 5.31 | 15.51 | | 1 | 43.97 | | 5.56 | 15.77 | |
| 4 | 43.37 | −0.18 | 4.86 | 14.97 | 0.72 | 4 | 44.23 | 0.25 | 5.28 | 15.33 | 0.58 |
| 8 | 45.18 | 1.63 | 4.94 | 15.29 | 1.68 | 8 | 46.23 | 2.26 | 5.23 | 16.36 | 2.36 |
| 12 | 45.58 | 2.03 | 4.71 | 15.58 | 2.11 | 12 | 49.24 | 5.26 | 4.85 | 16.52 | 5.36 |
| 24 | 47.99 | 4.43 | 5.01 | 16.7 | 4.6 | 24 | 50.37 | 6.40 | 5.05 | 16.74 | 6.49 |

In both cases the initial wash for Medium Brown Test and Medium Brown Comparative, respectively, was read against the successive washes. The above results illustrate that the hair swatches colored with the Medium Brown Test composition exhibit improved wear as the ΔL is less after 4, 8, 12, and 24 washes (less change in lightness or darkness) when compared to the ΔL after 4, 8, 12, and 24 washes in swatches treated with the Medium Brown Comparative composition. Thus, the hair swatches treated with Medium Brown Test composition had less color wash out (e.g. more fade resistance) than the hair swatches treated with Medium Brown Comparative composition. Similarly, the ΔE in the hair swatches treated with Medium Brown Test composition was significantly less when compared with the ΔE in the hair swatches treated with Medium Brown Comparative composition, thus illustrating that the total change in color after multiple washings in the Medium Brown Test composition is significantly less. Thus, the composition provides a hair color with less wash out hence more fade resistance.

EXAMPLE 5

Ten grams of the Medium Brown Test composition and the Medium Brown Comparative composition were applied to 1.5 gram samples of yak hair. Yak hair was used because of its pure white color, which enables color deposit and wash out to be more easily assessed. Five swatches per composition were treated. The compositions were applied to the hair for 10 minutes and rinsed with water. One swatch colored with each composition was shampooed using Revlon Flex Extra Body shampoo for 30 seconds once, and the others 4, 8, 12, and 24 times respectively. The swatches were compared visually and the values for L, ΔL, E, ΔE, a, and b were determined as set forth in Example 4, above. The results are as follows:

|  | Medium Brown Test | | | | Medium Brown Comparative | | | | |
|---|---|---|---|---|---|---|---|---|---|
| Wash | L | a | b | Wash | L | a | b | ΔL | ΔE |
| 1 | 28.8 | 7.2 | 8.17 | 1 | 30.62 | 8.14 | 10.08 | 1.82 | 2.8 |
| 4 | 31.66 | 6.96 | 8.21 | 4 | 31.31 | 7.51 | 8.66 | −0.35 | 0.79 |
| 8 | 31.62 | 7.11 | 8.47 | 8 | 35.55 | 7.25 | 9.89 | 3.93 | 4.18 |
| 12 | 32.58 | 6.76 | 8.19 | 12 | 36.03 | 7.36 | 9.83 | 3.45 | 3.87 |
| 24 | 36.87 | 6.33 | 8.2 | 24 | 39.52 | 6.82 | 8.92 | 2.66 | 2.79 |

In the above test results, the difference in L and E were compared between the yak hair swatches colored with Medium Brown Test composition and Medium Brown Comparative composition. For example, after 1 wash the difference in L and E values between the yak hair sample colored with Medium Brown Test composition and Medium Brown Comparative composition was calculated. The results illustrate that the yak hair swatches dyed with the Medium Brown Test Composition exhibited improved wear over 24 shampoos (reduced fade resistance and reduced wash out) when compared against the yak hair swatches dyed with Medium Brown Comparative Composition.

EXAMPLE 6

Ten grams of the light auburn hair color composition of Example 1 ("Auburn Test") and the light auburn hair color composition ("Auburn Comparative") of Example 2 were applied to yak hair swatches weighing 1 5 grams each. Five swatches per composition were treated. The compositions were applied to the hair for 10 minutes and rinsed with water. One swatch colored with each composition was shampooed using Revlon Flex Extra Body shampoo for 30 seconds once, and the others 4, 8, 12, and 24 times respectively. The swatches were compared visually and the values for L, ΔL, E, ΔE, a, and b were determined as in Example 4.

|  | Auburn Test | | | | Auburn Comparative | | | | |
|---|---|---|---|---|---|---|---|---|---|
| Wash | L | a | b | Wash | L | a | b | ΔL | ΔE |
| 1 | 40.51 | 22.83 | 28.29 | 1 | 40.14 | 22.08 | 24.71 | −0.37 | 3.88 |
| 4 | 45.18 | 21.34 | 29.88 | 4 | 48.03 | 19.05 | 28.08 | 2.85 | 4.08 |
| 8 | 49.11 | 19.45 | 30.29 | 8 | 51.12 | 17.85 | 28.94 | 2.01 | 2.9 |
| 12 | 52.34 | 18.51 | 31.39 | 12 | 54.99 | 15.62 | 29.32 | 2.65 | 4.44 |
| 24 | 57.2 | 15.6 | 30.83 | 24 | 57.95 | 14.02 | 28.57 | 0.75 | 2.86 |

In the above test, the values for L and E were computed by comparing the difference in L between yak hair swatches colored with Auburn Test composition and yak hair swatches colored with Auburn Comparative composition Then ΔE was calculated. The above results show that the Auburn Test Compositions exhibited better wear, reduced fade resistance, and reduced wash out when compared with the Auburn Comparative compositions. It also appears that color deposit was slightly better in the yak hair swatches treated with Auburn Test composition.

EXAMPLE 7

Ten grams of the dark brown/black hair color composition of Example 1 ("Black Test") and the dark brown/black comparative hair color composition ("Black Comparative") of Example 2 were applied to 95% gray hair swatches weighing 1.5 grams each. Five swatches per composition were treated. The compositions were applied to the hair for 10 minutes and rinsed with water. One swatch colored with each composition was shampooed once, and the others 4, 8, 12, and 24 times respectively. The values for L, ΔL, E, ΔE, a, and b were determined as in Example 4. The results are set forth below:

|  | Black Test | | | | | | Black Comparative | | | |
|---|---|---|---|---|---|---|---|---|---|---|
| Wash | L | ΔL | a | b | ΔE | Wash | L | ΔL | a | b | ΔE |
| 1 | 33.55 |  | 8.28 | 14.16 |  | 1 | 36.45 |  | 7.85 | 15.27 |  |
| 4 | 33.69 | 0.14 | 7.71 | 13.66 | 0.77 | 4 | 36.08 | −0.37 | 8.00 | 15.14 | 0.42 |
| 8 | 34.76 | 1.21 | 7.8 | 14.22 | 1.3 | 8 | 37.73 | 1.28 | 7.91 | 15.33 | 1.28 |
| 12 | 35.48 | 1.93 | 8.07 | 14.77 | 2.04 | 12 | 39.21 | 2.76 | 8.19 | 15.99 | 2.87 |
| 24 | 37.58 | 4.03 | 8.19 | 14.97 | 4.11 | 24 | 41.13 | 4.68 | 7.62 | 16.88 | 4.95 |

In the above tests, the 4, 8, 12, and 24 wash swatches were compared with the 1 wash swatch in the swatches treated with Black Test and Black Comparative compositions. The above tests show that the swatches treated with Black Test composition exhibited reduced fade resistance and wash out as well as improved color deposition when compared with the Black Comparative swatches after 1, 4, 8, 12, and 24 shampoos.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A method for restoring color to dyed hair strands that have faded, or applying color to new hair growth, comprising contacting said faded or discolored or new hair growth with a hair color composition comprising, in a polar solvent, association structures in the form of nematic or smectic liquid crystals having contained therein at least one water soluble or water dispersible semi-permanent dye wherein the liquid crystals are formed by the combination of one or more nonionic surfactants in a polar solvent which is a water and at least mono-, di-, or polyhydric alcohol and where in the composition is applied to faded hair strands or new hair growth from one to six weeks after the hair has been oxidatively colored and the composition additionally contains one or more fatty alcohols.

2. The method of claim 1 wherein the composition is applied to faded or discolored strands, or new hair growth, two to four weeks after the hair has been oxidatively dyed.

3. The method of claim 1 wherein the composition is applied to dry hair.

4. The method of claim 1 wherein the composition is in a multiple use container.

5. The method of claim 1 wherein the composition is in a single use container.

6. The method of claim 1 wherein the composition is applied to dry hair and after ten minutes shampooed out.

7. The method of claim 1 wherein the hair color composition comprises at least one water soluble or water dispersible semi-permanent dye selected from the group consisting of basic dye, HC dye, direct dye, disperse dye, acid dye, and mixtures thereof.

8. The method of claim 1 wherein the water soluble or water dispersible semi-permanent dye is present ranging from about 0.001–20% by weight of the total composition.

9. The method of claim 1 wherein the water soluble or water dispersible semi-permanent dye is selected from the group consisting of HC dyes, disperse dyes, and mixtures thereof.

10. The method of claim 1 wherein the water is present ranging from about 0.1–99.9% by weight of the total composition.

11. The method of claim 1 wherein the liquid crystals are smectic lyotropic liquid crystals in lamellar configuration.

12. The method of claim 11 wherein the liquid crystals are present ranging from about 0.01–100% by weight of the total composition.

* * * * *